United States Patent
Bader et al.

(10) Patent No.: US 7,186,755 B2
(45) Date of Patent: Mar. 6, 2007

(54) NIMESULIDE GEL SYSTEMS FOR TOPICAL USE

(75) Inventors: Stefano Bader, Milan (IT); Enrique Häusermann, Milan (IT); Tiziana Monti, Pazzallo-Lugano (CH)

(73) Assignee: Helsinn Health Care S.A., Pazzallo-Lugano (CH)

( * ) Notice: Subject to any disclaimer, the term of this patent is extended or adjusted under 35 U.S.C. 154(b) by 694 days.

(21) Appl. No.: 10/254,862

(22) Filed: Sep. 26, 2002

(65) Prior Publication Data

US 2003/0036563 A1    Feb. 20, 2003

Related U.S. Application Data

(63) Continuation of application No. 09/380,044, filed as application No. PCT/EP98/00990 on Feb. 20, 1998, now abandoned.

(30) Foreign Application Priority Data

Feb. 25, 1997    (IT)    .............................. MI97A0408

(51) Int. Cl.
| | | |
|---|---|---|
| A61K 31/18 | (2006.01) | |
| A61K 31/785 | (2006.01) | |
| A61K 31/795 | (2006.01) | |
| A61K 9/70 | (2006.01) | |

(52) U.S. Cl. ...................... 514/605; 514/769; 514/887; 424/78.05; 424/449

(58) Field of Classification Search ................ 514/605, 514/769, 887; 424/78.05, 449
See application file for complete search history.

(56) References Cited

U.S. PATENT DOCUMENTS

| 5,716,609 A | 2/1998 | Jain et al. | |
|---|---|---|---|
| 5,837,735 A * | 11/1998 | Miyata et al. | .............. 514/605 |

FOREIGN PATENT DOCUMENTS

| EP | 0 532 900 | 3/1993 |
|---|---|---|
| EP | 0 812 587 | 12/1997 |
| WO | 9611002 | 4/1996 |
| WO | WO 98/01124 | 1/1998 |

OTHER PUBLICATIONS

Chemical Abstracts, vol. 125, No. 4, Jul. 22, 1996, (abstract only) WIPO patent WO 9611002A Dec. 1997.
Chemical Abstracts, Database WPI/Derwent AN:97-225967 (abstract only) WIPO patent WO 9712608, Apr. 1997.

* cited by examiner

*Primary Examiner*—Vickie Kim
(74) *Attorney, Agent, or Firm*—Young & Thompson

(57) ABSTRACT

The present invention relates to nimesulide topical formulations comprising a carboxyvinylpolymer neutralized as a gel-forming agent or a polyacrylamide-isoparaffin and a solvent selected from the group consisting of ethanol, isopropanol and diethylene glycol monoethyl ether, and to the process for the preparation thereof. Said formulations have advantages such as higher stability of the system and bioavailability of the active ingredient.

10 Claims, No Drawings

NIMESULIDE GEL SYSTEMS FOR TOPICAL USE

This application is a continuation of application Ser. No. 09/380,044, filed on Oct. 7, 1999 now abandoned. Application Ser. No. 09/380,044 is the national phase of PCT International Application No. PCT/EP98/00990 filed on Feb. 20, 1998 under 35 U.S.C. §371. The entire contents of each of the above-identified applications are hereby incorporated by reference.

The present invention relates to nimesulide topical formulations based on gel systems.

Nimesulide is a known antiinflammatory agent whose therapeutical efficacy has been proved for some time, but which has the drawback of having unfavourable chemical-physical characteristics; the main obstacle to the use of nimesulide in topical formulations is in fact its insolubility in water and, on the other hand, its poor solubility in the solvents/raw materials usually employed in such formulations.

Some formulations of nimesulide for the external use are described in WO 96/11002; said formulations consist in dispersions of particles of the active ingredient throughout a component which, in the case of creams, comprises a hydrophilic polymer, an oily substance, a surfactant agent, a basic substance and water.

The application mentions no gel systems, in particular those in which the active ingredient is dispersed in solvents different from water; moreover the formulations proposed in WO 96/11002 do not solve some problems relating to the stability of the system and to the bioavailability of the active ingredient.

It has now been found that the combination of a gel based on carboxyvinylpolymer or other suitable gel-forming agents with a dispersion or nimesulide in solvents selected from ethanol, isopropanol or diethylene glycol monoethyl ether, gives significant advantages both in terms of stability of the system and of release and absorption of the active ingredient, therefore improving bioavailability.

The gel-forming action is obtained preferably through neutralization of the carboxyvinylpolymer resin in the acidic form, which chemically behaves as a weak acid; as regards the base to employ in the neutralization, the use of weak bases such as triethanolamine or diisopropanolamine, in a 1:1 acid/base equivalent ratio, turned out to be particularly successful.

The carboxyvinylpolymer used in the gelling process, such as carbomer, is obtained starting from acrylic/methacrylic acid, and it is used in amounts ranging from 0.1% to 5% by weight, preferably 0.5%–2.5%. Alternatively, a polyacrylamide-isoparaffin known under the commercial name Sepigel (Sepic), in amounts ranging from 0.5 to 10% by weight, can be used advantageously as the gel-forming agent.

The use of non aqueous solvents in the preparation of the gel systems of the invention, involves undoubtable advantages both in terms of chemical-physical characteristics and of release and absorption properties of nimesulide. In particular, the invention relates to the use of the solvents ethanol, isopropanol and diethylene glycol monoethyl ether, the latter proving to be particularly effective in increasing the absorption of the active ingredient, thanks to its solvent effect on the lipidic dermal barrier.

Said solvent effect, which although promoting the absorption of nimesulide could affect adversely the dermal hydratation, is compensated by the film- and touch-forming properties of the gel based on carboxyvinylpolymer.

Viscosity and pH of the compositions of the present invention can vary within wide ranges: from a few cps to above 100.000 as regards viscosity, whereas the preferred pH range is from 5 to 7. The amount of water can range from 40% to 95% by weight, whereas the amount of solvent, also depending on its contribute to the evaporation of the aqueous phase, is comprised from 5% to 20% by weight for ethanol and isopropanol, preferably about 10%; on the other hand, as far as diethylene glycol monoethyl ether is concerned, the diffusion and permeation properties thereof are related to concentrations from 5% to 40% by weight, preferably about 15%.

The active ingredient nimesulide can be dispersed in a wide range of concentrations, preferably from 0.5% to 7% by weight.

The compositions of the invention can also contain lipophilic excipients, such as caprylic or capric esters, or gliceryl (8)0E, which are capable of improving both the absorption and the final spreadability and "skin-feel" characteristics.

Appropriate preservant systems and lipophilic raw materials suitable for limiting any undesired effects caused by delipidization of the solvent at a superficial level can further be used.

The preservant system provides a microbiological protection by means of wide spectrum antimicrobials, such as imidazolidinyl urea and a balanced parabens mixture; a further guarantee of stability is the presence or a sequestrating agent such as EDTA which is capable of chelating any dangerous ions to keep an appropriate viscosity index.

Considering the high percentage of water present, it should be reminded that EDTA warrants an enhancing effect on the preservant system against microorganisms.

The compositions of the invention can further comprise emollients/humectants, such as cetyl esters 1–15% by weight, cholesterol 0.3–0.5% by weight, glycerin 1–30% by weight, isopropyl myristate 1–10% by weight, isopropyl palmitate 0.05–5.5% by weight, lecithin 1–20% by weight, lanolin alcohols 0.5–15% by weight, vaseline 4–95% by weight, soy lipids 1–20% by weight, as well as dermal absorption enhancers such as 2-pyrrolidone 0.1–10% by weight, propylene glycol 5–50% by weight, pyrrolidone derivatives 0.1–10% by weight.

The compositions of the invention can be prepared according to a process comprising:
  preparation of the dispersed phase containing the carboxyvinylpolymer gel-forming agent;
  addition of the alcoholic solvent, dispersion of the active ingredient nimesulide, addition of preservatives and stabilizing agents;
  neutralization of the resin with the selected base.

In the case of systems in which diethylene glycol monoethyl ether is the solvent, the process scheme can be exemplified as follows:
  preparation of the aqueous phase containing the water-soluble preservatives and the carboxyvinylpolymer homogeneously dispersed;
  preparation of the phase containing the preservatives (parabens) in diethylene glycol monoethyl ether and dispersion of the active ingredient. Addition of the phase consisting of caprylic/capric esters and glyceryl (8)0E;
  preparation of the dispersion, suspending the phase containing the active ingredient in the aqueous phase containing the carboxyvinylpolymer;
  preparation of the stabilizers suitably solubilized in the aqueous phase;
  neutralization of the resin with the selected base.

The compositions of the invention have the following advantages:
- capability of solubilizing nimesulide;
- rapidity and release mechanism of the gel carrier;
- capability of promoting absorption;
- reduction of induced dehydration phenomena.

The compositions of the invention proved to be well tolerated, both in animals (rabbit and guinea pig) and in clinical studies.

The efficacy of the compositions of the invention has been tested using well-known pharmacological tests, such as the UV-induced erythema in guinea pigs, the croton oil-induced inflammation of the guinea pig ear, the carrageenin-induced granuloma in the rat.

The dermal adsorption has been studied using $^{14}C$ nimesulide both in rats and in human volunteers, no significant systemic concentrations of nimesulide being observed in either of these cases.

The compositions of the invention were also clinically tested on 200 patients affected with tendinitis of the upper limb or with benign ankle sprains, according to a controlled, double-blind experimental design.

The compositions of the invention turned out to be effective in a statistically significant way, in comparison with placebo.

The following are examples of some preparations obtained with the process of the invention:

EXAMPLE 1

| Phase | Ingredient | % w/w |
|---|---|---|
| Phase A | Purified water | q.s. |
|  | Imidazolidinyl urea | 0.20 |
|  | EDTA tetrasodium salt | 0.10 |
| Phase B | Carbomer (CARBOPOL 1382) | 1.20 |
| Phase C | Mix parabens | 0.20 |
|  | Vaseline | 1.00 |
| Phase D | Isopropanol | 10.00 |
| Phase E | Nimesulide | — |
| Phase F | Purified water | 10.00 |
|  | Triethanolamine | 0.60 |

The formulation was prepared at four nimesulide concentrations, i.e. 2, 3, 4, 5% w/w, each concentration in 3 different 5 kg batches Phase A+B, i.e. the dispersion of Carbopol in the solution of water and preservatives, was obtained by swelling the gel for two days at room temperature until reaching a homogeneous dispersion. Phase C was prepared in a Gianke & Kunkel Type PM43 paddle mixer heated on a water bath.

After the addition of isopropanol, the homogenization was carried out with a Guarniero Mantelli Type F43CV2 homogenizer.

Alternatively, the whole preparation can be performed dispersing Carbopol in water by means of a turbine under vacuum, mixing with paddles after addition of phase C and homogenizing again with the turbine under vacuum after addition of isopropanol.

Paracombin, a powder mixture of methyl, ethyl, propyl, butyl p-hydroxybenzoates, was used as preservative. Methyl, ethyl and propyl p-hydroxybenzoates are cited in Italian Pharmacopoeia XI ed. Butyl p-hydroxybenzoate is cited in USP XXIII.

This mixture was added with the preservative imidazolidinyl urea.

EXAMPLE 2

|  | % w/w |
|---|---|
| Water | 83.40 |
| Ethanol | 10.00 |
| Nimesulide | 3.00 |
| Carbomer (CARBOPOL 1382) | 1.40 |
| Petrolatum | 1.00 |
| Triethanolamine | 0.70 |
| Imidazolidinyl urea | 0.20 |
| Methyl, ethyl, propyl parabens | 0.20 |
| Tetrasodium EDTA | 0.10 |

| Chemical-physical-characteristics | At preparation | After 45 days at room temp. | After 45 days at temp. = 40° C. |
|---|---|---|---|
| Aspect | Opaque white gel | Opaque white gel | Opaque white gel |
| pH | 5.00 | 5.03 | 4.98 |

No traces of separation or decrease in viscosity were observed.

EXAMPLE 3

|  | % w/w |
|---|---|
| Water | 83.40 |
| Isopropanol | 10.00 |
| Nimesulide | 3.00 |
| Carbomer (CARBOPOL 1382) | 1.40 |
| Petrolatum | 1.00 |
| Triethanolamine | 0.60 |
| Imidazolidinyl urea | 0.20 |
| Methyl, ethyl, propyl parabens | 0.20 |
| Tetrasodium EDTA | 0.10 |

| Chemical-physical-characteristics | At preparation | After 45 days at room temp. | After 45 days at temp. = 40° C. |
|---|---|---|---|
| Aspect | Opaque white gel | Opaque white gel | Opaque white gel |
| pH | 5.00 | 5.03 | 5.01 |

No traces of separation or decrease in viscosity were observed.

EXAMPLE 4

| Phase | Ingredient | % w/w |
|---|---|---|
| Phase A | Purified water | q.s. |
|  | Glyceryl (8)OE Caprylate/Caprinate | 2.00 |
|  | Imidazolidinyl urea | 0.20 |
|  | EDTA tetrasodium salt | 0.10 |
| Phase B | Carbomer (CARBOPOL 940) | 1.00 |
| Phase C | Mix parabens | 0.20 |
|  | Diethylene glycol monoethyl ether | 15.00 |
|  | Nimesulide | — |
| Phase D | Purified water | 10.00 |
|  | Triethanolamine | 0.50 |

The formulation was prepared at four nimesulide concentrations, i.e. 2%, 3%, 4%, 5% w/w, each concentration in 3 different 5 kg batches.

EXAMPLE 5

|  | % w/w |
| --- | --- |
| Water | 83.40 |
| Diethylene glycol monoethyl ether | 15.00 |
| Nimesulide | 3.00 |
| Carbomer (CARBOPOL 940) | 1.00 |
| PEG-8 Caprylic/capric glycerids | 2.00 |
| Triethanolamine | 0.50 |
| Imidazolidinyl urea | 0.20 |
| Methyl, ethyl, propyl parabens | 0.20 |
| Tetrasodium EDTA | 0.10 |

| Chemical-physical-characteristics | At preparation | After 45 days at room temp. | After 45 days at temp. = 40° C. |
| --- | --- | --- | --- |
| Aspect | Opaque white gel | Opaque white gel | Opaque white gel |
| pH | 5.20 | 5.18 | 5.21 |

No traces of separation or decrease in viscosity were observed.

The invention claimed is:

1. Nimesulide topical formulations in the form of gel systems comprising carboxyvinylpolymer neutralized with aqueous solutions of weak bases or a polyacrylamideisoparaffin and 5–40% by weight of a solvent selected from the group consisting of ethanol, isopropanol, diethylene glycol monoethyl ether, said formulations comprising nimesulide dispersed in said solvent, and said formulations having a water content from 40–95% by weight.

2. Formulations according to claim 1, in which ethanol and isopropanol are used at a concentration ranging from 5% to 20% by weight.

3. Formulations according to claim 2, in which said concentration is 10% by weight.

4. Formulations according to claim 1, in which said concentration is 15%.

5. Formulations according to claim 1, in which the weak base used for the neutralization of the carboxyvinylpolymer is triethanolamine or diisopropanolamine.

6. Formulations according to claim 1, in which the active ingredient nimesulide is dispersed in a concentration range of 0.5–7% by weight.

7. Formulations according to claim 1, further comprising additives selected from the emollients, humectants, absorption enhancers, preservatives.

8. Formulations according to claim 7, in which the preservatives are imidazolidinyl urea, parabens and EDTA.

9. A process for the preparation of the formulations of claim 1 which comprises:
preparation of the dispersed phase containing the carboxyvinylpolymer gel-forming agent;
addition of the alcoholic solvent, dispersion of the active ingredient nimesulide, addition of preservatives and stabilizing agents;
neutralization of the resin with the selected base.

10. A process for the preparation of the formulations of claim 1 which comprises:
preparation of the aqueous phase containing the water-soluble preservatives and the carboxyvinylpolymer homogeneously dispersed;
preparation of the phase containing the preservatives (parabens) in diethylene glycol monoethyl ether and dispersion of the active ingredient and addition of phase consisting of caprylic/capric esters and glyceryl (8) 0E;
preparation of the dispersion, suspending the phase containing the active ingredient in the aqueous phase containing the carboxyvinylpolymer;
preparation of the stabilizers suitably solubilized in the aqueous phase;
neutralization of the resin with the selected base.

* * * * *